United States Patent [19]

Boschelli et al.

[11] Patent Number: 5,143,927
[45] Date of Patent: Sep. 1, 1992

[54] 3-(THIAZOLIDONE, OXAZOLIDINONE, IMIDAZOLIDINONE)-INDOLES AS ANTIINFLAMMATORY AGENTS

[75] Inventors: Diane H. Boschelli, Plymouth; David T. Connor, Ann Arbor, both of Mich.

[73] Assignee: Warner-Lambert Company, Morris Plains, N.J.

[21] Appl. No.: 697,823

[22] Filed: May 9, 1991

[51] Int. Cl.$^5$ .................. C07D 417/06; A61K 31/425
[52] U.S. Cl. ........................ 514/369; 548/181; 548/225; 548/226; 548/309; 548/318
[58] Field of Search .................. 548/181; 514/369

[56] References Cited

U.S. PATENT DOCUMENTS

| | | | |
|---|---|---|---|
| 499,937 | 3/1890 | Cetenko et al. | 548/181 |
| 3,161,654 | 12/1964 | Shen et al. | 548/181 |
| 4,464,382 | 8/1984 | Tanouchi et al. | 548/181 |

FOREIGN PATENT DOCUMENTS 89109406.2 of 0000 European Pat. Off. .
279263 8/1988 European Pat. Off. .

OTHER PUBLICATIONS

Derwent Abstract 86-059691/09 Japanese Pat. App. J61012-674-A.
Derwent Abstract 87-307841/44 Denmark Pat. App. 3713-094-A.
International Journal of Sulfur Chemistry, vol. 2, No. 1, 1972, pp. 261-266, T. R. Bosin et al.

*Primary Examiner*—Robert Gerstl
*Attorney, Agent, or Firm*—Joan Thierstein

[57] ABSTRACT

The present invention is for selected novel compounds which are 3-[thiazolidinone, oxazolidinone, imidazolidinone]-indoles as well as pharmaceutical compositions and methods of use thereof. These compounds have activity useful in treating allergies and inflammation.

10 Claims, No Drawings

3-(THIAZOLIDONE, OXAZOLIDINONE, IMIDAZOLIDINONE)-INDOLES AS ANTIINFLAMMATORY AGENTS

BACKGROUND OF THE INVENTION

The present invention is novel compounds which are indoles substituted at the 3-position with thiazolidinone, oxazolidinone, or imidazolidinones, and pharmaceutically acceptable acid addition or base salts thereof, pharmaceutical compositions and methods of use thereof. The invention compounds are now found to have activity as inhibitors of one or both of cyclooxygenase and 5-lipoxygenase providing treatment of conditions advantageously affected by such inhibition including inflammation, arthritis, pain, fever, and the like. Thus, the present invention is also a pharmaceutical composition or method of use thereof.

Although indoles are known antiinflammatory agents and various 2 substituted thiazolidinones, oxazolidinones, or imidazolidinones are known as useful substituents in other antiinflammatory agents, for example, with 3,5-di-tertiary-butyl-4-hydroxyphenyl groups as disclosed in EP Application No. 89 109406.2 and U.S. patent application Ser. No. 499,937 (incorporated herein by reference), the present combination of ring systems, substituents and moieties is not among those previously known. Other compounds having ring systems including various thiazolidinones, oxazolidinones, and imidazolidinones and references disclosing such related compounds are found in the following references as well as:

Japanese patent application J6 1012-674-A (Derwent Abstract 86-059691/09) discloses an imidazolidinone compound of the structure

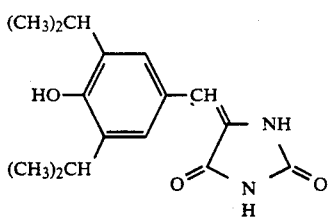

with utility as an antiallergic. It lacks the indole structure present in the compounds claimed herein.

Denmark Patent Application DE 3713-094-A (Derwent Abstract 87-307841/44) discloses benzylidene compounds of which compounds of the structure

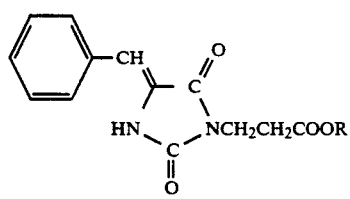

are included, wherein R is 1-18C straight chain alkyl or 3-18C branched or cyclic alkyl. These compounds lack the indole structure present in the compounds claimed herein.

U.S. Pat. No. 4,464,382 discloses compounds of the formula

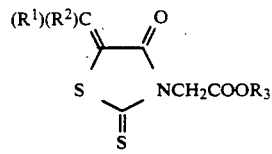

wherein (1) $R^1$ and $R^2$ are taken together to represent a tetramethylene or pentamethylene group, (II) $R^1$ represents a hydrogen atom, and $R^2$ represents (1) a cycloalkyl or cycloalkenyl group of 4-7 carbon atoms which is unsubstituted or substituted by at least one alkyl group of 1-4 carbon atoms, (2) an anthryl or naphthyl group, (3) a phenyl group which is unsubstituted or substituted, p. 2 (4) a heterocyclic group containing at least one of nitrogen, oxygen, and sulfur atoms which is unsubstituted or substituted (5) a

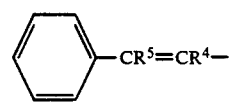

group (wherein $R^4$ represents a hydrogen atom, a halogen atom, phenyl group, or an alkyl group of 1-5 carbon atoms; and $R^5$ represents a hydrogen atom, a phenyl group, or an alkyl group of 1-5 carbon atoms) or

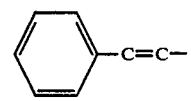

group; or (III) $R^1$ and $R^2$, which may be the same or different with each other, each represents a phenyl group which is unsubstituted or substituted; and $R^3$ represents a hydrogen atom, an alkyl group of 1-12 carbon atoms, an aralkyl group of 7-13 carbon atoms, a cycloalkyl or cycloalkenyl group of 4-7 carbon atoms which is unsubstituted or substituted by at least one alkyl group of 1-4 carbon atoms, or a phenyl group which is unsubstituted or substituted, possess a strong inhibitory activity on aldose reductase but lack the indole structure.

Bosin and Campaigne, *Intnt'l. J. of Sulfur Chem.*, Vol. 2, p. 262 (1972) disclose compounds of the formula

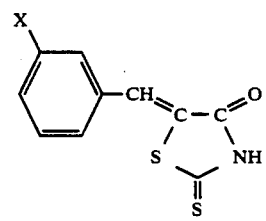

wherein X is F or Cl. These compounds also lack the indole structure of the present invention.

Compounds are disclosed having an indole system substituted at the 2- or 3-position in European Publication Number 279,263 and U.S. Pat. No. 4,464,382.

U.S. Pat. No. 3,161,654 discloses an indole ring system substituted through the nitrogen with p-chlorobenzoacyl.

These compounds may be distinguished from the compounds of the invention herein by the absence of oxazolidinone, imidazolidinone, or thiazolidinone structures or by the unique combination of indole substituents disclosed here.

Within these disclosures are uses for treating inflammation as are found here, but the differences between known compounds and the present compounds are readily apparent, with no teaching to make obvious that such differences would also be useful for treatment of the conditions taught here.

Thus, the disclosed compounds do not contain the combination of ring systems and substituents which is the present invention.

SUMMARY OF THE INVENTION

The present invention is a compound of the formula (I)

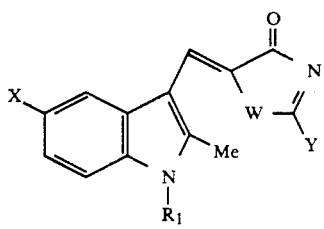

or a pharmaceutically acceptable salt thereof; wherein
(1) $R_1$ is hydrogen, lower alkyl, acyl which is

wherein $R_4$ is lower alkyl, phenyl, or substituted phenyl; or (2) X is hydrogen, hydroxyl, chlorine, bromine, fluorine, iodine, or O-lower alkyl;

(3) Y is
  (a) $NH_2$;
  (b) $SR_2$ wherein $R_2$ is lower alkyl or $CH_2COOR_3$ wherein $R_3$ is hydrogen or lower alkyl;
  (c) $S(O)_nR_2$ wherein n is 1 or 2 and $R_2$ is as defined above;
  (d) $NR_2R_3$ wherein $R_2$ and $R_3$ are as defined above;
  (e) NHCN;
  (f) $NHC(A)NHR_3$ wherein A is oxygen, sulfur, or NH and $R_3$ is as defined above;
  (g) $NR_3(OR_3)$ wherein $R_3$ is as defined above;
  (h) $NHNHC(S)NH_2$;
  (i) $NHNHC(NH)NH_2$;

(4) W is oxygen, sulfur, or $NR_3$ wherein $R_3$ is as defined above;

(5) Me is methyl.

The present invention is also a compound of the formula (II)

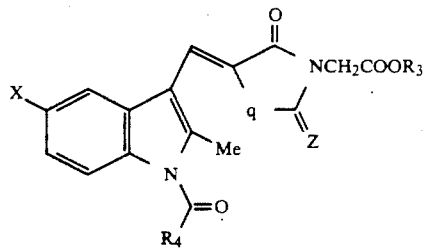

or a pharmaceutically acceptable salt thereof; wherein
(1) X, $R_3$, and $R_4$ are as defined above;
(2) Z is oxygen, sulfur, or NH;
(3) q is oxygen or sulfur;

The present invention is also a pharmaceutical composition for the treatment of conditions advantageously affected by the inhibition of one or both 5-lipoxygenase and cyclooxygenase which comprises an amount effective for the treatment of the condition of a compound of formula I or formula II and the pharmaceutically acceptable salt thereof together with a pharmaceutically acceptable carrier. Compounds of this invention are inhibitors of the synthesis of the products of one or both of the enzymes 5 lipoxygenase and cyclooxygenase, and are for the treatment of the conditions meant to include rheumatoid arthritis, osteoarthritis, other inflammatory conditions, psoriasis, pain, allergic diseases, asthma, inflammatory bowel disease, GI ulcers, cardiovascular conditions including ischemic heart disease and atherosclerosis, and ischemia-induced cell damage, particularly brain damage caused by stroke. These conditions can also include acne, sunburn, psoriasis, and eczema. Such conditions are exemplary in nature and are in no way meant to limit the scope of the invention.

The present invention is also a method for treatment of the condition as noted above in a mammal, including humans, suffering therefrom with a compound of formula I or formula II or a pharmaceutically acceptable acid addition or base salt thereof, in unit dosage form. The invention also provides for use of any such compound of formula I or II or salt thereof in the manufacture of a medical therapeutic agent.

Pharmaceutical composition or use of the compound or salt of formula I or formula II is meant to include treatment understood to be prophylactic pertinent to the foregoing named conditions.

The most preferred compound of the present invention is a compound of the formula I wherein W is sulfur; Y is $SCH_3$; $R_1$ is H; X is H or $OCH_3$.

DETAILED DESCRIPTION OF THE INVENTION

In compounds of formula I or II, the term "lower alkyl" includes an alkyl group of from one to six carbons such as methyl, ethyl, propyl, butyl, and the like and isomers thereof. The term "substituted phenyl" is a phenyl substituted by from one to three of lower alkyl, lower alkoxy, hydroxy, halogen, trifluoromethyl, $NO_2$, mercapto, lower alkylthio, $NR_{10}R_{11}$ wherein $R_{10}$ and $R_{11}$ are independently hydrogen or lower alkyl.

The compounds of formula I where Y is $NH_2$, NHCN, $NHC(A)NHR_3$, $NHNHC(S)NH_2$, and $NHNHC(NH)NH_2$, wherein A and $R_3$ are as defined above, can exist as tautomers. These tautomers are represented as I and I':

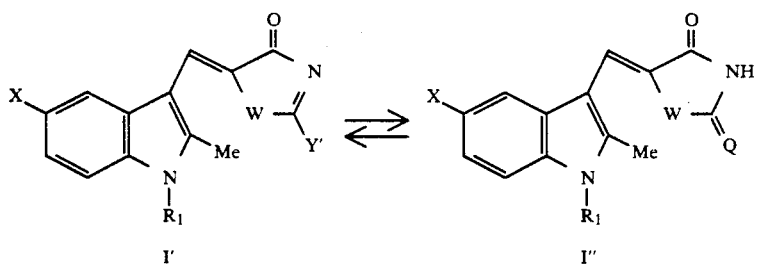

wherein Y' is NH$_2$, NHCN, NHC(A)NHR$_3$, NHNHC(S)NH$_2$, NHNHC(NH)NH$_2$, and Q is NH, NCN, NC(A)NHR$_3$, NNHC(S)NH$_2$, respectively, or NNHC(NH)NH$_2$ and W, X, Me, and R$_1$ are as defined above.

Appropriate compounds of formula I or II are useful in free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid and benzenesulfonic acid, p-toluenesulfonic acid, and the like, giving the hydrochloride, sulfamate, ethanesulfonate, benzenesulfonate, p-toluenesulfonate, and the like, respectively; or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di- , and trialkylamines such as methylamine, dimethylamine, and triethylamine; mono- , di- , or trihydroxyalkylamines such as mono- , di- , or triethanolamine; amino acids such as arginine and lysine; chlorine; guanidine; N-methyl glucosamine; n methyl glucamine; l-glutamine; N-methylpiperazine; morpholine; ethylene diamine; N-benzylphenethylamine; tris(hydroxymethyl)-aminoethane; and the like (see for example, "Pharmaceutical Salts", *J. Pharm. Sci.* 66(1):1–19 (1977)). Salts of inorganic bases include sodium, potassium, calcium, or the like.

The acid addition salts of said basic compounds are prepared either by dissolving the free base or acid of compound I or II in an aqueous or aqueous alcohol solution or other suitable solvent containing the appropriate acid or base, and isolating the salt by evaporating the solution or by reacting the free base of compound I or II with an acid as well as reacting compound I or II having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

The compounds of this invention may also exist in hydrated or solvated forms.

Thus, pharmaceutical compositions are prepared from compounds of formula I and II and salts thereof described as the present invention in unit dosage form comprising the compound either alone or in admixture with a pharmaceutically acceptable carrier appropriately selected from those known.

In determining when a lipoxygenase, cyclooxygenase, or dual lipoxygenase/cyclooxygenase inhibitor is indicated, of course, inter alia, the particular condition in question and its severity, as well as the age, sex, weight, and the like of the subject to be treated must be taken into consideration and this determination is within the skill of the attending physician or veterinarian.

A physician or veterinarian of ordinary skill readily determines a subject who is exhibiting allergic or inflammatory symptoms. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, cachets, lozenges, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an unaffected area (e.g., in the form of eye drops or by inhalation). For the treatment of allergic or inflammatory conditions such as erythema, the compounds of the present invention may also be administered topically in the form of ointments, creams, gels, or the like. In general, the preferred route of administration is orally.

An effective but nontoxic quantity of the compound of formula I or II or pharmaceutically acceptable salt thereof is employed in treatment. The dosage regimen is selected according to a variety of factors including condition of the subject to be treated, severity of symptoms, and the route of administration. In so proceeding, the physician or veterinarian could employ relatively low dosages at first, subsequently increasing the dose until a maximum response is obtained. For convenience, the total daily dosage may be divided and administered in portions during the day if desired.

Initial dosages of the compounds of the invention having formula I or II or pharmaceutically acceptable salt thereof are ordinarily in the range of 20 mg up to 25 g per day, orally, preferably 50 mg to 350 mg per dose orally, given from one to four times daily or as needed. When other forms of administration are employed, equivalent doses are administered.

A suitable dose of a compound of formula I or II or pharmaceutically acceptable salt thereof for a subject suffering from any condition as described herein before is 0.1 μg to 500 mg of the compound per kilogram body weight. In the case of systemic administration, the dose may be in the range of 0.5 to 500 mg of the compound per kilogram body weight, the most preferred dosage being 0.5 to 500 mg per kilogram body weight administered two to three times daily. In the case of topical administration, e.g., to the skin or eye, a suitable dose may be in the range of 0.1 ng to 100 μg of the compound per kilogram body weight, typically about 0.1 μg/kg.

In the case of oral dosing for the treatment of prophylaxis of arthritis or inflammation in general, due to any cause, a suitable dose of a compound of formula I or II or a pharmaceutically acceptable salt thereof, may be as specified in the preceding paragraph, but most preferably is from 1 to 5 mg of the compound per kilogram of body weight, for example, from 1 to 2 mg per kilogram body weight.

While it is possible for an active ingredient to be administered alone, it is preferable to present it as a pharmaceutical formulation comprising a compound of formula I or II or a pharmaceutically acceptable acid addition or base salt thereof and a pharmaceutically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The usefulness of the compounds of the present invention as inhibitors of the 5 lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air 5% carbon dioxide. Cells are harvested by centrifugation. They are washed with cold phosphate buffered saline, pH 7.4 (PBS; NaCl, 7.1 g; $Na_2HPO_4$, 1.15 g; $KH_2PO_4$, 0.2 g; and KCl, 0.2 g/L). Cells are finally suspended in PBS containing 1.0 mM calcium at a density of $2\times10^6$ cells/mL. Cells are incubated and without test agent (in DMSO) (1% DMSO is without effect on arachidonic acid metabolism) for 10 minutes at room temperature. Calcium ionophore A23187 (5 μM) is added and cells are incubated for 7 minutes at 37° C. The reaction is stopped by chilling the tubes on ice for 10 minutes. Cells are separated by centrifugation and the supernatant is stored at −20° C. Aliquots (100 μL) are analyzed for $LTB_4$ and $PGF_{2\alpha}$ using radioimmunoassay kits as provided by the supplier.

Table 1 contains biochemical data for compounds of formula I obtained from this whole cell assay as amount of inhibition at 10 μM or $IC_{50}$s which are calculated as the concentration of a test compound in micromoles (μM) causing 50% inhibition of $LTB_4$ or $PGF_{2\alpha}$ formation.

TABLE 1

| Example | ARBL[a] | ARBC[b] |
| --- | --- | --- |
| 1 | 8.23[c] | 0.29[c] |
| 2 | N[d] | N[d] |
| 3 | 4.43[c] | 0.14[c] |
| 4 | 90% | 60% |
| 5 | 48% | N[d] |

[a] Inhibition of $LTB_4$
[b] Inhibition of $PGF_{2\alpha}$
[c] $IC_{50}$
[d] N = Less than 40% inhibition at 10 μM In addition to the compounds of formula I or II, or a pharmaceutically acceptable salt thereof, the pharmaceutical compositions can also contain other active ingredients, such as cyclooxygenase inhibitors, nonsteroidal antiinflammatory drugs (NSAIDs), peripheral analgesic agents such as zomepirac, diflunisol, and the like. The weight ratio of the compound of the formula I or II to the second active ingredient may be varied and will depend upon the effective dose of each ingredient. Generally, an effective dose of each will be used. Thus, for example, when a compound of the formula I or II or salt thereof is combined with an NSAID, the weight ratio of the formula I or II or salt thereof to the NSAID will generally range from about 100:1 to about 1:1000, preferably about 200:1 to 1:200. Combinations of a compound of the formula I or II and other active ingredients will generally also be within the aforementioned range, but in each case, an effective dose of each active ingredient should be used.

Combinations of a compound of the formula I or II or salt thereof and other active ingredients will generally be in the aforementioned ratios.

NSAIDs can be characterized into five groups:

(1) the propionic acid derivatives;
(2) the acetic acid derivatives;
(3) the fenamic acid derivatives;
(4) the biphenylcarboxylic acid derivatives and
(5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flubiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free $-CH(CH_3)CCOH$ or $-CH_2CH_2COOH$ group (which optional only can be in the form of a pharmaceutically acceptable salt group, e.g., $-CH(CH_3)COO^{13}Na^+$ or $-CH_2CH_2COO^{-Na+}$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, ioxepac, furofenac, tropinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —$CH_2COOH$ group (which optionally can be in the form of a pharmaceutically acceptable salt group, e.g., —$CH_2COO^-Na^+$) typically attached directly to a ring system, preferably to an aromatic or heteroaromatic ring system.

Thus, "fenamic acid derivatives" as defined herein are nonnarcotic analgesics/nonsteroidal antiinflammatory drugs which contain the basic structure:

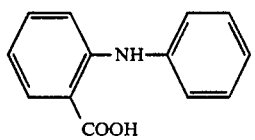

which can bear a variety of substituents and in which the free —COOH group can be in the form of a pharmaceutically acceptable salt group, e.g., —$COO^-Na^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

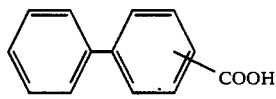

which can bear a variety of substituents and in which the free —COOH group can be in the form of a pharmaceutically acceptable salt group, e.g., —$COO^-Na^+$.

The oxicams which can be used in the present invention comprise: piroxicam, sudoxicam, isoxicam, and 4-hydroxy 1,2 -benzothiazine 1,1 -dioxide 4 -(N-phenyl)-carboxamide. Structurally related oxicams having similar analgesic and antiinflammatory properties are also intended to be encompassed by this group.

Thus, "oxicams" as defined herein are nonnarcotic analgesic/nonsteroidal antiinflammatory drugs which have the general formula:

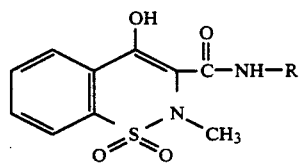

wherein R is an aryl or heteroaryl ring system.

The following NSAIDs may also be used: acemetacin, aminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emcrfazone, enfenamic acid, enolicam, epirizole, etersalate, etodolac, etofenamate, fenetizole mesylate, fenclofenac, fenclorac, fendosal, fenflumizole, fentiazac, feprazone, floctafenine, flunixin, flunoxaprofen, fluproquazone, fopirtoline, fosfosal, furcloprofein, furofenac, flucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate, sodium, meseclazone, microprofen, nabumetone, nictinodole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudixocam, suprofen, talmetacin, talniflumate, tenoxicam, thiazolinobutazine, thielavin B, tiaprofenic acid, tiaramide HCl, tiflamazole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I or II compound or salt thereof may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compound of formula I or II or salt thereof may also be advantageously combined with an $H_1$ or $H_2$ -receptor antagonist, such as for instance, cimetidine, ranitidine, terfenadine, famotidine, temelastine, acrivastine, loratidine, utrizine, tazifylline, azelastine, aminothiadiazoles disclosed in European Patent 81102976.8 and like compounds such as those disclosed in U.S. Pat. No. 4,283,408; 4,362,736; 4,394,508; and European Patent Application 40,696. The pharmaceutical compositions may also contain a $K^+/H^+$-ATPase inhibitor such as omeprazole, disclosed in U.S. Pat. No. 4,255,431, and the like. Each of the references referred to in this paragraph is hereby incorporated by reference.

Generally, the scheme for the preparation of the compounds of formula I above is as follows:

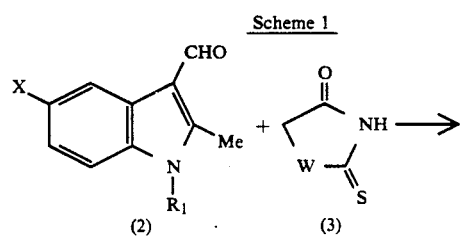

-continued
Scheme 1

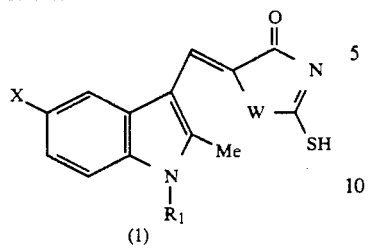

(1)

wherein X, Me, R₁, and W are as defined above.

That is, a general method of preparation of these compounds is condensation of the aldehyde (2) with a compound having an active methylene group (3). This condensation can be performed in an alcoholic solvent such as ethanol, methanol, or the like in the presence of either a base such as ammonia or piperidine or with a catalytic amount of a mineral acid such as sulfuric acid, HCl, or the like. Alternatively, acetic acid is used as the solvent with either anhydrous sodium acetate or preferably α-alanine. The reactants are heated at reflux for several hours.

Subsequent treatment with R₂-halide wherein R₂ is as defined above, but preferably iodomethane, in the presence of an inorganic or organic base, preferably diisopropylethylamine, in an etheral solvent such as dioxane or preferably an alcoholic solvent such as methanol, gives compounds of the formula

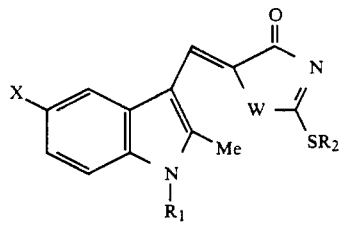

(4)

wherein X, W, Me, R₁, and R₂ are as defined above.

Subsequent treatment of compounds of formula (4) with an oxidizing agent, preferably m-CPBA, provides compounds of formula I where $Y=S(O)_nR_2$ wherein n and $R_2$ are as defined above. One equivalent of oxidizing agent provides compounds where $Y=S(O)R_2$; two equivalents of oxidizing agent provides compounds where $Y=S(O)_2R_2$.

Compounds of formula I wherein $Y=NR_2R_3$, NHCN, NHC(A)NHR₃, NR₃(OR₃), NHNHC(S)NH₂, or NHNHC(NH)NH₂ wherein A, R₂, and R₃ are as defined above are generated by treatment of compound (4) with the corresponding amine in an alcoholic solvent, preferably t-butanol, in the presence or absence of potassium t-butoxide at elevated temperatures. Alternatively, these compounds are generated by heating compound (4) and the corresponding amine in a solvent such as DMF or the like.

Finally, compounds of formula I where $Y=NH_2$ are obtained by condensation of the aldehyde (2) with a compound of formula (5)

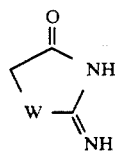

wherein W is as defined above.

A general method for the preparation of compounds of formula II is as follows:

Scheme 2

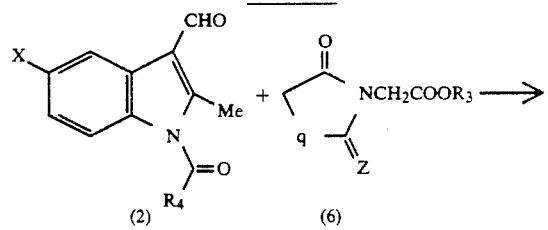

wherein X, q, Z, R₃, R₄, and Me are as defined above. This condensation can be performed in an alcoholic solvent in the presence of either a base such as ammonia or piperidine or with a catalytic amount of a mineral acid such as H₂SO₄, HCl, or the like. Alternatively, acetic acid is used as the solvent with either anhydrous sodium acetate or preferably β-alanine. The reactants are heated at reflux for several hours.

Conditions within the description of Schemes 1 and 2 above and variations in the description are known or can be readily determined from analogous reactions known to one of ordinary skill in the art.

Those compounds that contain an acidic proton can be converted to salts via treatment with an organic or inorganic base.

Generally, starting materials are known, commercially available, or can be prepared by known methods. In particular, see U.S. Pat. No. 4,981,865.

Under certain circumstances as discussed above, it is necessary to protect either the N or 0 of intermediates. Introduction and removal of such suitable oxygen and nitrogen protecting groups are well known in the art of organic chemistry; see for example, "Protective Groups in Organic Chemistry," J. F. W. McOmie, Advances in Organic Chemistry 3:159–190 (1963); J. F. W. McOmie, Chem. & Ind. 603 (1979), and T. W. Greene, "Protective Groups in Organic Synthesis," Wiley (New York) 1981, Chapters 2, 3, and 7.

Examples of suitable oxygen protecting groups are benzyl, t-butyl-protecting groups, ethoxyethyl, methoxyethoxymethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethyl carbamate, trichloroethoxycarbonyl, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis and t-butyldimethylsilyl being removed by reaction with, for example, tetra-n butylammonium fluoride.

In the process described herein for the preparation of compounds of this invention, the requirements for protective groups are generally well recognized by one skilled in the art of organic chemistry, and accordingly the use of appropriate protecting groups is necessarily implied by the processes of the schemes herein, although not expressly illustrated.

The products of the reactions described herein are isolated by conventional means such as extraction, distillation, chromatography, and the like.

The invention is further elaborated by the representative examples as follows. Such examples are not meant to be limiting.

EXAMPLE 1

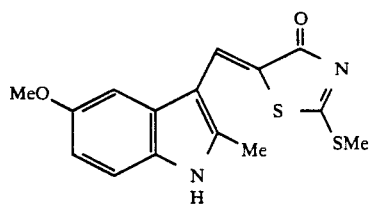

(Z) -5-[(5 -Methoxy-2 -methyl-1H -indol-3-yl)methylene]-2 -(methylthio)-4(5H)-thiazolone To a room temperature suspension of (Z)-5-[(5 -methoxy- 2-methyl-1H -indol -3-yl)methylene]-2-thioxo-4-thiazolidinone (1.714 g, 5.63 mmols) in 50 mL of methanol is added Hunig's base (1.15 mL, 6.61 mmols) followed by iodomethane (0.500 mL, 8.03 mmols). The thick suspension is stirred overnight at room temperature. Filtration washing with ether provides 1.631 g (91%) of (Z)-5-[(5-methoxy-2-methyl-1H-indol-3-yl)methylene]-2-(methylthio)-4-(5H)-thiazolone; mp 214°-222° C. dec. Calc'd for $C_{15}H_{14}N_2O_2O_2S_2$:
C, 56.58; H, 4.43; N, 8.80; S, 20.14.
Found: C, 56.44; H, 4.35; N, 8.63; S, 20.48.

EXAMPLE 2

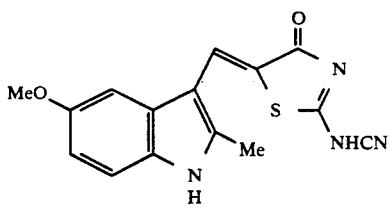

(Z)-[4,5-Dihydro-5-[(5 -methoxy-2-methyl-1H-indol-3-yl)methylene]-4-oxo-2-thiazolyl]-cyanamide To a room temperature suspension of potassium t-butoxide (73 mg, .65 mmols) and cyanamide (96 mg, 2.27 mmols) in 10 mL of t-butanol is added (Z)-5-[(5-methoxy-2-methyl-1H-indol-3-yl)methylene]-2-(methylthio)- 4(5H)-thiazolone (146 mg, 0.46 mmols). The mixture is heated at reflux for 5 minutes, then cooled to room temperature. The mixture is poured into 50 mL of water and the orange solution is washed with diethyl ether. The layers are separated and the aqueous layer is acidified with 10% aqueous hydrochloric acid. The orange solid is collected by filtration, washing with water to give 106 mg (74%) of (Z)- [4,5-dihydro-5-[(5-methoxy-2-methyl-1H-indol-3-yl)methylene]-4-oxo-2-thiazolyl]cyanamide; mp >300.

Calc'd for $C_{15}H_{12}N_4O_2S$: C, 57.68; H, 3.87; N, 17.94.
Found: C, 57.53; H, 3.96; N, 17.75.

EXAMPLE 3

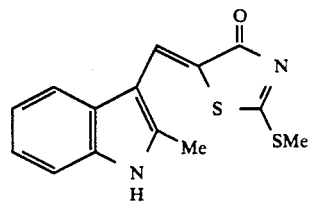

(Z) -5-[(2-Methyl-1H-indol-3-yl)methylene]-2-(methylthio)-4(5H)-thiazolone

To a room temperature suspension of (Z) -5-[(2-methyl-1H-indol-3-yl)methylene]-2-thioxo-4-thiazolidinone (1.502 g, 5.48 mmols) in 50 mL of methanol is added Hunig's base (1.15 mL, 6.61 mmols) followed by iodomethane (.500 mL, 8.03 mmols). The thick suspension is stirred for 2 hours at room temperature. Filtration washing with 1:1 hexane:ether provides 1.201 g of an orange solid. This material is suspended in 100 mL of hot ethyl acetate and filtered to provide 943 mg (60%) of (Z) -5-[(2 -methyl-1H-indol-3-yl)methylene]-2-(methylthio)-4(5H)-thiazolone; mp 253°-255° C. dec.

Calc'd for $C_{14}H_{12}N_2OS_2$: C, 58.31; H, 4.19; N, 9.71.
Found: C, 58.02; H, 4.13; N, 9.65.

EXAMPLE 4

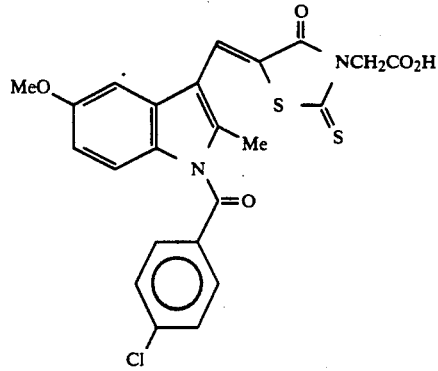

(Z)-5-[[1-(4-Chlorobenzoyl)-5-methoxy-2-methyl-1H-indol-3-yl]methylene]-4-oxo-2-thioxo-3-thiazolidine acetic acid To a room temperature solution of 1-(4-chlorobenzoyl)-5-methoxy-2 methylindole-carboxaldehyde (535 mg, 1.63 mmols) and rhodanine 3-acetic acid (345 mg, 1.80 mmols) in 15 mL of acetic acid is added β-alanine (142 mg, 1.59 mmols). The solution is heated at reflux for 1.5 hours, then allowed to cool to room temperature. Filtration, washing with acetic acid, then hexane, provides 458 mg (56%) of (Z)-5-[[1-(4 chlorobenzoyl)-5-methoxy-2-methyl-1H -indol-3-yl]methylene]-4-oxo-2-thioxo-3-thiazolidine acetic acid as a yellow solid. An analytical sample is obtained by two recrystallizations from acetonitrile: mp 204°–208° C.

Calc'd for $C_{23}H_{17}ClN_2O_5S_2$: C, 55.14; H, 3.42; N, 5.59.

Found: C, 54.83; H, 3.46; N, 5.89.

EXAMPLE 5

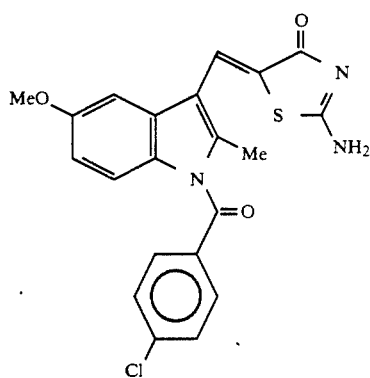

(Z)-5-[[1-(4-Chlorobenzoyl)-5-methoxy-2-methyl-1H-indol-3-yl]methylene]-2-imino-4-thiazolidinone To a room temperature solution of 1-(4-chlorobenzoyl)-5-methoxy-2 -methylindole-carboxaldehyde (517 mg, 1.58 mmols) and pseudothiohydantoin (743 mg, 6.41 mmols) in 15 mL of acetic acid is added β-alanine (147 mg, 1.65 mmols). The solution is heated at reflux for 2.5 hours, then allowed to cool to room temperature. One drop of water is added and stirring is continued for 1 hour. Filtration provides 179 mg (27%) of (Z)-5-[[1-(4-chlorobenzoyl)-5-methoxy-2 -methyl-1H-indol-3-yl]methylene]-2 -imino 4 thiazolidinone as an orange solid. An analytical sample is obtained by recrystallization from acetonitrile; mp 269°–270° C.

Calc'd for $C_{21}H_{16}ClN_3O_3S$: C, 59.22; H, 3.79; N, 9.86.

Found: C, 59.00; H, 3.46; N, 9.89.

We claim:

1. A compound of the formula (I)

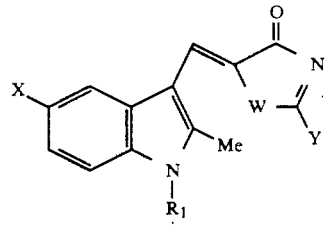

or a pharmaceutically acceptable salt thereof; wherein
(1) $R_1$ is hydrogen, lower alkyl or

wherein $R_4$ is lower alkyl, phenyl, or phenyl substituted by from one to three of lower alkyl, lower alkoxy, hydroxy, halogen, trifluoromethyl, $NO_2$, mercapto, lower alkylthio, $NR_{10}R_{11}$ wherein $R_{10}$ and $R_{11}$ are independently hydrogen or lower alkyl;
(2) X is hydrogen, hydroxyl, chlorine, bromine, fluorine, iodine, or O-lower alkyl;
(3) Y is
 a) $NH_2$;
 b) $SR_2$ wherein $R_2$ is lower alkyl or $CH_2COOR_3$ where $R_3$ is hydrogen or lower alkyl;
 c) $S(O)_nR_2$ wherein n is 1 or 2 and $R_2$ is as defined above;
 d) $NR_2R_3$ wherein $R_2$ and $R_3$ are as defined above;
 e) NHCN;
 f) NHC(A)NHR_3 wherein A is oxygen, sulfur, or HN and $R_3$ is as defined above;
 g) $NR_3$ $(OR_{3a})$ wherein $R_3$ is as defined above and $R_{3a}$ is hydrogen or lower alkyl;
 h) $NHNHC(S)NH_2$;
 i) $NHNHC(NH)NH_2$;
(4) W is sulfur;
(5) Me is methyl.

2. A compound of claim 1 which is (Z)-5-[(5-methoxy-2-methyl-1H-indol-3-yl)methylene]-2-(methylthio)-4(5H)-thiazolone.

3. A compound of claim 1 which is (Z)-[4,5 dihydro-5-[(5-methoxy-2-methyl-1H-indol-3-yl)methylene]-4-oxo-2-thiazolyl]-cyanamide.

4. A compound of claim 1 which is (Z)-5-[(2-methyl-1H-indol 3 yl)methylene]-2-(methylthio)-4(5H)-thiazolone.

5. A compound of claim 1 which is (Z)-5-[[1-(4-chlorobenzoyl) -5-methoxy-2-methyl-1H-indol-3-yl]methylene]-2-imino-4-thiazolidinone.

6. A pharmaceutical composition for treating inflammation comprising an antiinflammatory amount of a compound of claim 1 with a pharmaceutically acceptable carrier.

7. A method of treating inflammation in a subject suffering therefrom comprising administration of a compound of claim 1 in a unit dosage form.

8. The compound (Z)-5-[[1-(4-chlorobenzoyl)-5-methoxy-2-methyl-1H-indol-3-yl]methylene-4-oxo-2-thioxo-3-thiazolidine acetic acid or a pharmaceutically acceptable salt thereof.

9. A pharmaceutical composition for treating inflammation comprising an antiinflammatory amount of a compound of claim 8 with a pharmaceutically acceptable carrier.

10. A method of treating inflammation in a subject suffering therefrom comprising administration of a compound of claim 8 in a unit dosage form.

* * * * *